US012298291B2

(12) United States Patent
    Zhu (10) Patent No.: US 12,298,291 B2
(45) Date of Patent: May 13, 2025

(54) NITROGEN SENSOR APPARATUS FOR SIMULTANEOUSLY MEASURING NITRATE/NITRITE AND AMMONIUM IN WASTEWATER AND METHOD OF OPERATING SAME

(71) Applicant: THE RESEARCH FOUNDATION FOR THE STATE UNIVERSITY OF NEW YORK, Albany, NY (US)

(72) Inventor: Qingzhi Zhu, Stony Brook, NY (US)

(73) Assignee: THE RESEARCH FOUNDATION FOR THE STATE UNIVERSITY OF NEW YORK, Albany, NY (US)

(*) Notice: Subject to any disclaimer, the term of this patent is extended or adjusted under 35 U.S.C. 154(b) by 116 days.

(21) Appl. No.: 17/908,282

(22) PCT Filed: Mar. 2, 2021

(86) PCT No.: PCT/US2021/020374
    § 371 (c)(1),
    (2) Date: Aug. 31, 2022

(87) PCT Pub. No.: WO2021/178345
    PCT Pub. Date: Sep. 10, 2021

(65) Prior Publication Data
    US 2023/0088167 A1    Mar. 23, 2023

Related U.S. Application Data

(60) Provisional application No. 62/983,911, filed on Mar. 2, 2020.

(51) Int. Cl.
    *G01N 33/18*    (2006.01)

(52) U.S. Cl.
    CPC .................... *G01N 33/188* (2013.01)

(58) Field of Classification Search
    CPC .................................... G01N 33/188
    See application file for complete search history.

(56) References Cited

U.S. PATENT DOCUMENTS 3,579,298 A    5/1971    George
3,723,308 A    3/1973    Breck
               (Continued)

FOREIGN PATENT DOCUMENTS

CA    1258360 A    8/1989
DE    3009724 A1   9/1980
      (Continued)

OTHER PUBLICATIONS

Extended European Search Report dated Nov. 30, 2023, received in a corresponding foreign application, namely European Patent Application No. 21764081, 9 pages.
(Continued)

*Primary Examiner* — John E Breene
*Assistant Examiner* — Alex T Devito
(74) *Attorney, Agent, or Firm* — Scully, Scott, Murphy & Presser, P.C.

(57) ABSTRACT

A detection system and method for simultaneously determining the concentration of ammonium and nitrate/nitrite in samples such as surface water and wastewater. The detection system and method herein can further comprise a cleaning loop and a calibration loop and can be used in situ and over long periods of time without replacement or frequent maintenance and upkeep.

28 Claims, 4 Drawing Sheets

(56) References Cited

U.S. PATENT DOCUMENTS

| | | |
|---|---|---|
| 4,512,794 A | 4/1985 | Eastin |
| 4,515,615 A | 5/1985 | Eastin |
| 4,602,928 A | 7/1986 | Eastin |
| 5,871,620 A | 2/1999 | Haug et al. |
| 6,039,783 A | 3/2000 | Lueck et al. |
| 6,090,267 A | 7/2000 | Hansen et al. |
| 6,641,638 B1 | 11/2003 | Lueck et al. |
| 7,655,473 B2 | 2/2010 | Golitz |
| 2012/0261335 A1* | 10/2012 | Lemaire .......... C02F 3/006 210/96.1 |
| 2012/0315209 A1 | 12/2012 | Bisson et al. |
| 2012/0318734 A1 | 12/2012 | Galgon et al. |
| 2013/0256217 A1* | 10/2013 | Lemaire .......... C02F 3/26 210/96.1 |
| 2015/0274541 A1 | 10/2015 | Jeppson et al. |
| 2016/0067652 A1 | 3/2016 | Moore, Jr. |
| 2016/0299090 A1 | 10/2016 | Jensen et al. |
| 2017/0050872 A1 | 2/2017 | Scroggins |
| 2020/0299166 A1 | 9/2020 | Boudreaux et al. |
| 2021/0162343 A1 | 6/2021 | Koers |

FOREIGN PATENT DOCUMENTS

| | | | |
|---|---|---|---|
| DE | 69617911 T2 | | 9/2002 |
| DE | 69807253 T2 | | 3/2003 |
| DE | 202011000946 | * | 9/2011 |
| DE | 102011017032 A1 | | 10/2012 |
| EP | 0148967 B1 | | 4/1991 |
| EP | 0766651 A1 | | 4/1997 |
| EP | 2500082 A1 | | 9/2012 |
| EP | 2942098 A1 | | 11/2015 |
| EP | 3831463 B1 | | 9/2023 |
| EP | 4114800 B1 | | 2/2025 |
| ES | 2197996 T3 | | 1/2004 |
| ES | 2902723 A1 | | 3/2022 |
| GB | 2269895 B | | 9/1996 |
| JP | S59174520 A | | 10/1984 |
| JP | S60166292 A | | 8/1985 |
| JP | H08197076 | * | 8/1996 |
| JP | 2012505138 A | | 3/2012 |
| KR | 20120040146 A | | 4/2012 |
| KR | 20140090099 | * | 7/2014 |
| MX | 2012001813 A | | 10/2012 |
| NL | 8001532 A | | 9/1980 |
| WO | 2011017707 A1 | | 2/2011 |
| WO | 2011107984 A2 | | 9/2011 |
| WO | 2012145118 A1 | | 10/2012 |
| WO | 2016100903 A2 | | 6/2016 |
| WO | 2017223372 A1 | | 12/2017 |
| WO | 2020237283 A1 | | 12/2020 |

OTHER PUBLICATIONS

Nunez, L., et al., "Development and application of an electronic tongue for detection and monitoring of nitrate, nitrite and ammonium levels in waters", Microchemical Journal, Apr. 2013, pp. 273-279, 110.

International Search Report dated May 19, 2021 issued in PCT/US2021/020374.

Baquerizo et al., "A detailed model of a biofilter for ammonia removal: Model parameters analysis and model validation", Chemical Engineering Journal 113 (2005), pp. 205-214.

Hall, P.O.J. et al., "Rapid Small-Volume Flow Injection Analysis for TCO2 and NH4+ in Marine and Freshwaters" Limnol. Oceanogr. (1992), vol. 37 No. 5, pp. 1113-1119.

Written Opinion dated May 19, 2021 issued in PCT/US2021/020374.

Choosang, J., et al., "Simultaneous Detection of Ammonium and Nitrate in Environmental Samples Using on Ion- Selective Electrode and Comparison with Portable Colorimetric Assays", Sensors 2018, Published: Oct. 19, 2018, 12 pages, 8, 3555.

Wang, C., et al., "A High-Performance Optoelectronic Sensor Device for Nitrate Nitrogen in Recirculating Aquaculture Systems", Sensors 2018, Published: Oct. 10, 2018, 16 pages, 18, 3382.

Boukhenane, M. L., et al., "Novel and Cost-efficient Sensors for the Concentration Measurement of Ammonia and Ammonium Nitrate Particles", Sensors & Transducers, Sep.-Oct. 2019, pp. 80-87, vol. 237, Issue 9-10.

Vrablova, M., et al., "Combined SPRi Sensor for Simultaneous Detection of Nitrate and Ammonium in Wastewater", Sensors 2021, Published: Jan. 21, 2021, 11 pages, 21, 725.

Australian Office Action dated Feb. 4, 2025, received in a corresponding foreign application, namely Australian Patent Application No. 2021230509, 2 pages.

* cited by examiner

NITROGEN SENSOR APPARATUS FOR SIMULTANEOUSLY MEASURING NITRATE/NITRITE AND AMMONIUM IN WASTEWATER AND METHOD OF OPERATING SAME

This application claims priority under 35 U.S.C. § 119 to provisional application U.S. Ser. No. 62/983,911, filed Mar. 2, 2020, the entire contents of which are incorporated herein by reference.

FIELD

The disclosure pertains to a detection system and method for the determining the concentration of ammonium and nitrate/nitrite in various settings, including without limitation water samples, such as surface water, ground water or wastewater samples from residential and commercial septic systems and municipal wastewater treatment plants.

BACKGROUND

Ammonium and nitrate/nitrite are the most common species of inorganic nitrogen in surface water, ground water and wastewater. Ammonium, nitrate/nitrite discharged from conventional residential septic systems can cause critical water quality problems and severe threats to public health. In coastal areas, septic systems are generally a major nitrogen pollution source. To protect public health, ecosystems and water resources, local and state regulators encourage the widespread installation of advanced septic systems, innovative and alternative onsite wastewater treatment systems (I/A OWTS), designed to remove significant amounts of nitrogen before releasing final effluent into ground water. How to accurately quantify, over a long period of time and in situ, ammonium and nitrate/nitrite in the effluents of I/A OWTS is crucial for ensuring proper functioning and performance of the I/A OWTS over the lifetime of the technologies, as well as for managing coastal freshwater and ocean systems.

Various nitrogen sensors based on optical methods and ion selective electrode (ISE) have been developed for nitrate, nitrite and ammonium measurements, but none of them are suitable for the long-term and in-situ measurements of nitrate, nitrite and ammonium in VA OWTS wastewater systems due to their high cost, high maintenance, and/or interferences by wastewater. Developing sensitive and selective nitrate and ammonium sensor package for in situ measurements and long-term deployments in wastewater with low-cost and low-maintenance is therefore a highly attractive goal.

SUMMARY

In one aspect the disclosure is directed to a detection system for simultaneously determining the concentration of ammonium, nitrate/nitrite in samples such as surface water, wastewater and the like. In one practice, the detection system comprises a sample loop having an internal flow path in fluid communication with a wastewater sample that comprises water, ammonium, nitrate/nitrite, and particulate matter. The sample loop, which can be formed of copper tubing or other anti-biofouling material, comprises a loop outlet in fluid communication with a feed conduit, a first one-way valve assembly, such as a check valve, configured to be open to the feed conduit, and a first pump assembly in fluid communication with the feed conduit. In the system, a first alkaline stream is in fluid communication with the feed conduit to mix the first alkaline solution with the wastewater sample and convert the ammonium to ammonia and generate a first stream. A first filter assembly is in fluid communication with the first stream to remove at least a portion of the particulate matter from the sample stream and generate a filtered first stream. A first gas-diffusion cell comprising a first acid solution feed for (i) removing the ammonia from the filtered first stream to generate second stream comprising the nitrate/nitrite and for (ii) converting the removed ammonia back to ammonium to generate a third stream comprising the ammonium is provided. A first conductivity detector assembly is employed for determining the concentration of ammonium in the third stream; and a plurality of reducing columns, wherein each reducing column individually comprises a reducing metal is provided to convert the nitrate/nitrite in the second stream to ammonia and to generate a fourth stream comprising the ammonia produced by reducing the nitrate/nitrite; in one practice, the plurality of reducing columns configured for parallel flow, and a valve assembly for each of the reducing columns is present and configured to open the flow of the second stream to the respective reducing columns one at a time, in a sequential fashion to each succeeding column. A second gas-diffusion cell comprising a second acid solution feed for (i) removing the ammonia produced by reducing the nitrate/nitrite in the fourth stream and (ii) converting the removed ammonia produced by reducing the nitrate/nitrite back to ammonium is provided to generate a fifth stream comprising the ammonium; and a second conductivity detector assembly is present to determine the concentration of ammonium in the fifth stream from which the concentration of the nitrate/nitrite is determined, the correlation being 1:1 (molar ratio).

In another aspect, the disclosure is directed to a method for simultaneously determining the concentration of ammonium, nitrate/nitrite in a sample comprising (a) providing a sample loop having an internal flow path and comprising a loop outlet in fluid communication with a feed conduit, and a first one-way valve assembly configured to be open to the feed conduit; (b) flowing a sample stream comprising water, ammonium, and nitrate/nitrate, and particulate matter, from the loop outlet through the feed conduit using a first pump assembly, the first one-way valve assembly being in an open position; (c) converting the ammonium in the sample stream to ammonia to form a first stream comprising the ammonia and the nitrate/nitrite; (d) flowing the first stream through a first filter assembly to remove at least a portion of the particulate matter from the first stream and generate a filtered first stream; (e) removing the ammonia from the filtered first stream to form a second stream comprising the nitrate/nitrite; (f) converting the removed ammonia back to ammonium to form a third stream comprising the ammonium and determining the concentration of ammonium in the third steam; and (g) reducing the nitrate/nitrite in the second stream to ammonia to form a fourth stream comprising the ammonia produced by reducing the nitrate/nitrite and converting the ammonia in the fourth stream to ammonium to form a fifth stream comprising the ammonium that was converted from the ammonia in the fourth stream, and determining the concentration of the ammonium in the fifth stream to determine to the concentration of the nitrate/nitrite.

In other aspects, the disclosure provides a detection system and method that allows for anti-biofouling and clog-free sampling, self-calibration, and nitrate/nitrite reduction with multiple redox columns that permit extended use. The detection system provides for in-situ, long-term deployment in wastewater systems of residential innovative and alternative onsite wastewater treatment systems (I/A OWTS) and/or municipal wastewater treatment plants, with low maintenance (e.g. no more than quarterly), remote operation and remote data transmission. The detection system evinces excellent liner response for both nitrate/nitrite and ammonium in the range of 2 to 70 N-mg/L nitrogen (which range is indicative of wastewater market requirements) with a detection limit of 1 N-mg/L. Moreover, the detection system can be remotely operated to measure hourly, daily, or any scheduled time with high accuracy (error <±20%) and precision (RSD <20%).

BRIEF DESCRIPTION OF THE DRAWINGS

In FIG. 3, one complete measurement cycle of 60 min is shown in which the running time is 58 min (0-58 min) and control board self-checking time is 2 min (59-60 min). The arrowed lines with "x" indicate which of the pump and valve assemblies as identified for the embodiment in FIG. 1 are off during the cycle; and the arrowed lines without an "x" indicate which pump and valve assemblies are on during the cycle.

DETAILED DESCRIPTION

The following detailed description of embodiments of the disclosure are made in reference to the accompanying figures. Explanation about related functions or constructions known in the art are omitted for the sake of brevity in understanding the concept of the invention to avoid obscuring the invention with unnecessary detail.

As used herein, "nitrate/nitrite" intends nitrogen oxide anion compounds of formula $NO_x^{-1}$ wherein X=2, 3 or both. Ammonium intends $NH_4^+$. Ammonium is a weak acid in water and can be converted to a moderately strong base, i.e., ammonia ($NH_3$), by reacting with a strong base solution, such as sodium hydroxide (NaOH) or potassium hydroxide (KOH). Ammonia in solution is a dissolved gas that can be separated from water solution by diffusing through a hydrophobic gas-permeable and liquid-impermeable membrane and be converted back to ammonium on the other side of the membrane by associating with a proton in acid solution.

The molar conductivity of free acid (free hydrogen ion) is 34.98 $mS/m^2/mol$, which is much higher than that of ammonium ion (7.34 $mS/m^2/mol$). Thus the association of ammonia with proton in acid solution causes the conductivity of acid solution to decrease, and the change of conductivity is proportional to the concentration of ammonia in the sample. Nitrate and nitrite in the water solution can be reduced to ammonia by means known in the art, e.g. a reduction column. Once the dissolved ammonia gas in sample solution is separated by diffusing through a gas-permeable membrane, the remaining nitrate and/or nitrite anions in the sample is then reduced to ammonia and determined by the same conductivity sensing principle discussed above.

Figure 1:
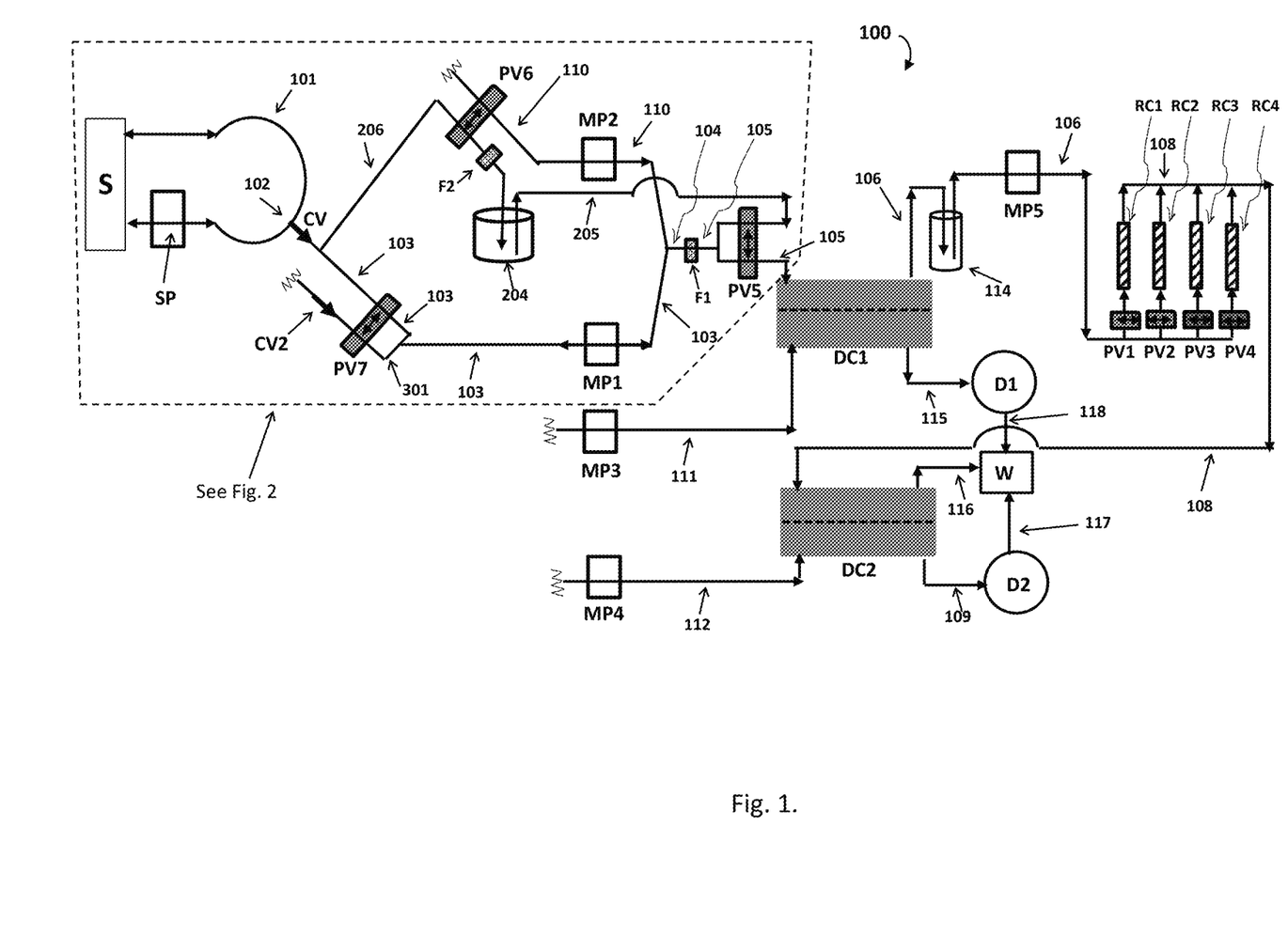
FIG. 1 is a schematic flow diagram for an embodiment of the method and system of the disclosure

Referring to FIG. 1, thereat is a schematic flow diagram depicting an embodiment of a detection system 100 and method of the disclosure. In this embodiment, a sample S of wastewater, comprising water, ammonium, nitrate/nitrite, and particulate matter, from a commercial or residential septic tank is pumped by first pump assembly SP into a sample loop 101 which has an internal flow path for the sample and which can be comprised of copper, e.g. copper tubing or other anti-biofouling material(s). The size of the copper tube can vary, e.g. 0.25 in. The sample loop has a loop outlet 102 (see also FIG. 2) in fluid communication with feed conduit 103, and a first one-way valve assembly CV which can be a check valve to permit flow into the feed conduit 103 but not back into the sample loop 101. The sample loop further comprises (see FIG. 2) a first loop opening 201 and a second loop opening 202 each in fluid communication with the sample source S and with first pump assembly SP, which first pump assembly can be configured to provide forward and reverse flow, wherein at least a portion of the forward flow provides sample from the first loop opening 201 to the loop outlet 102, and wherein at least a portion of the reverse flow provides sample from the second loop opening 202 to the loop outlet 102.

Figure 2:
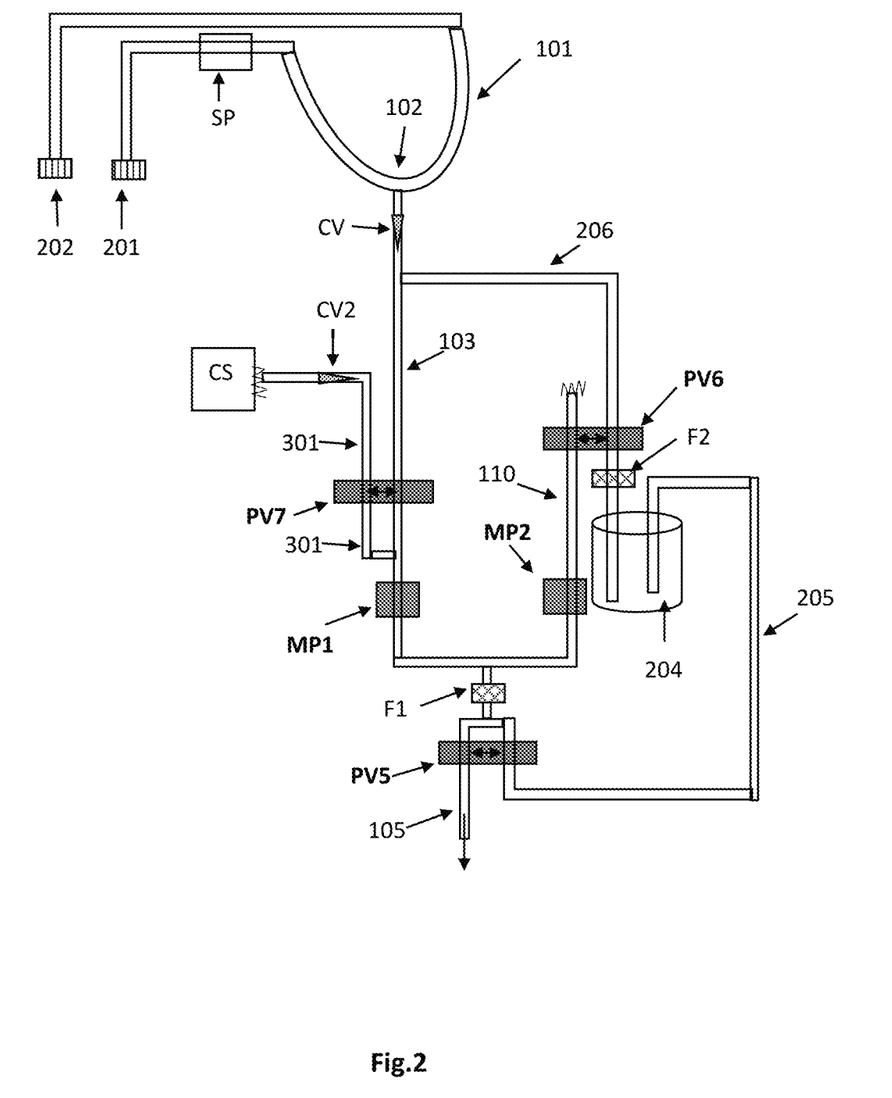
FIG. 2 is a detailed schematic flow diagram of an embodiment of the backflush cleaning loop embodiment and the self-calibration embodiment within the dotted line area identified in FIG. 1.

The first loop opening 201 and the second loop opening 202 can each individually comprise a copper screen to remove certain particulate matter from the sample source S, e.g. without limitation, copper screen of less than 100 mesh can be used.

In one practice, for a first portion a measurement cycle, e.g. for the first three minutes (t=03), SP is on and the first pump assembly MP1, which is in fluid communication with feed conduit 103, is off. Thus, no flow in sample loop 101 exits loop outlet 102 when SP is on. When SP is turned off, at the end of the first portion of this measurement cycle, e.g. a minute 3 (t=3), the first pump assembly is turned on and draws sample out of loop 101 and through loop outlet 102. Pump SP can be operated in forward or reverse flow during this initial portion of a cycle, when first pump assembly is off. In forward flow, sample is drawn from first loop opening 201 and exits the second loop opening 202 to remove particulate matter from the opposite side of the copper screen on second loop opening 202. Similarly, when SP is operated in reverse flow, sample drawn from second loop opening 202 and exits the first loop opening 201 to remove particulate matter from the opposite side of the copper screen on first loop opening 201.

In the embodiment shown, the ammonium in the sample stream is converted to ammonia by contacting the sample stream with an alkaline solution stream 110, e.g. a stream comprising NaOH, KOH, or both. The sample stream in feed conduit 103 mixes with the alkaline solution stream 110 which can be provided by second pump assembly MP2 from an alkaline solution source (not shown) the flow of which is controlled by third valve assembly PV6 to form first stream 104 which flows though a first filter assembly F1 to remove at least a portion of the particulate matter and to generate a filtered first stream 105.

The ammonia that was converted by contact with alkaline stream 110 is removed from the filtered first stream 105 by first gas-diffusion cell DC1, which such gas-diffusion cells are known in the art, and which also converts the ammonia it removes from the filtered first stream back to ammonium by contacting the ammonia with a first acid solution feed 111 provided by first acid pump MP3 comprising one or more acids such as without limitation thin oxalic acid, citric acid, HCl and the like. In one practice, DC1 comprises a gas permeable membrane, such as without limitation a hydrophobic expended PTFE membrane with pore size of 0.2-0.45 micrometer, which permits transfer of ammonia in the first filtered stream 105 from a first side of the membrane to a second side of the membrane, but not appreciable transfer of the nitrate/nitrite. The converted ammonium exits first gas-diffusion cell DC1 in third stream 115, and the nitrate/nitrite exit first gas-diffusion cell DC1 in second stream 106.

The concentration of ammonium in third stream 115 that exits DC1 is detected by means known in the art, e.g. by a conductivity detector. The ammonium so detected is the concentration of ammonium in the sample S from which the third stream 115 derives. In the practice shown, third stream 115 is flowed to a first conductivity detector D1 from which the ammonium concentration is detected. After detection, stream 118 flows from D1 to waste W.

The nitrate/nitrite in the second stream 106 is reduced to ammonia to form a fourth stream 108. In one practice, the nitrate/nitrite in the second stream 106 is reduced by feeding the second steam 106 to a plurality of reducing columns, RC1, RC2, RC3, RC4 (four reducing columns are depicted but more than four or less than four are contemplated). Each reducing column individually comprising a reducing metal as known in the art, e.g. granular zinc coated with 5% $CuSO_4$, to convert the nitrate/nitrite in the second stream 106 to ammonia to generate a fourth stream 108 comprising the ammonia produced by the reducing columns. The plurality of reducing columns can be configured for parallel flow (as depicted) wherein each of the reducing columns comprising a reducing column valve assembly, PV1, PV2, PV3, PV4, to open or stop the flow of the second stream 106 to any one of the respective reducing columns. In one practice, the reducing column valve assemblies are operated cycle the flow of the second stream 106 to one reducing column at a time, e.g. to RC1 for a pre-determined period of time whereafter the flow of 106 to RC1 is stopped and the flow to RC2 opens for another pre-determined period of time, and so on in sequence through all the reducing columns after which the flow of 106 to RC1 recommences. Such cycling permits longer operation of the detection system. In one non-limiting practice, second stream 106 is collected in an intermediate reservoir 114 wherefrom at least a portion of the collected second stream 106 is pumped by intermediate pump assembly MP5 to the plurality of reducing columns, RC1, RC2, R3, RC4. The use of intermediate reservoir 114 mitigates potential damage to the gas permeable membrane in DC1 under the pressure from the reducing columns.

The ammonia in the fourth stream 108 is flowed to second gas-diffusion cell DC2 wherein it is converted back to ammonium by contacting the ammonia in stream 108 with a second acid solution feed 112 provide by second acid pump MP4 which can comprise one or more acids such as without limitation thin oxalic acid, citric acid, HCl and the like. In one practice, DC2 comprises a gas permeable membrane, such as without limitation a hydrophobic expended PTFE membrane with pore size of 0.2-0.45 micrometer, which permits transfer of ammonia in the fourth stream 108 from a first side of the membrane to a second side of the membrane, but not appreciable transfer of the hydrated ions. DC2 can but need not be of the same design as DC1. The converted ammonium exits second gas-diffusion cell DC2 in fifth stream 109.

The concentration of ammonium in fifth stream 109 that exits DC2 is detected by means known in the art, e.g. by a conductivity detector. In the practice shown, fifth stream 109 exits DC2 and is flowed to second conductivity detector D2 from which the ammonium concentration is detected. After detection, stream 117 flows from D2 to waste W, as does stream 116. The ammonium detected in D2 is the equal to the concentration of nitrate/nitrite in the second stream 106, the molar ratio of detected ammonium to nitrate/nitrite in the second stream 106 is 1:1.

In another aspect, the system and method further comprise a recycle cleaning loop as depicted in FIG. 2. which is in fluid communication with the feed conduit 103 and the first filter assembly F1. The cleaning loop is configured to provide a reverse flow of a backflush solution through the first filter assembly F1 and the feed conduit 103, the first one-way valve assembly CV being in a position closed to reverse flow in 103. In one instance, the recycle cleaning loop comprises:

a reservoir 204 containing a backflush solution, such as without limitation an alkaline solution, e.g. 2.5% KOH, 2.5% NaOH or combinations thereof containing chelate such as without limitation a 1% of diethylenetriamine-pentaacetic acid (DPTA) or ethylenediaminetetraacetic acid (EDTA). A backflush feed conduit 205 is in fluid communication with the reservoir 204 and with the first filter assembly F1. A backflush recycle conduit 206 is in fluid communication with the feed conduit 103 and with the backflush reservoir 204, or with a recycle storage reservoir (not shown). A second valve assembly PV5 is configured to be open for the flow of the backflush solution from the backflush feed conduit 205 to the first filter assembly F1 during a cleaning cycle. A second filter assembly F2, which can be of large size, e.g. of 2-5 cm inner diameter, in fluid communication with the backflush recycle conduit 206 removes particulate matter from the backflush solution returning to the reservoir 204; a third valve assembly PV6 is configured to be open for the flow of backflush solution from the backflush recycle conduit 206 to the second filter assembly F2. A first pump assembly MP1 is in fluid communication with the backflush feed conduit 205 when the second valve assembly PV5 and the third valve assembly PV6 are in the open position, the first pump assembly MP1 configured to provide the reverse flow of the backflush solution through the feed conduit 103.

In one non-limiting cleaning operation, second and third valve assemblies PV5 and PV6 are open to permit flow of backflush solution from reservoir 204 through backflush feed conduit 205 and first filter assembly F1, the flow direction removing particulate matter from the side of F1 opposite the flow from 205, which flow traverses feed conduit 103 and into backflush recycle conduit 206 and second filter assembly F2 which removes the particulate and other matter collected from the first filter assembly F1 and feed conduit 103 before the backflush solution returns to reservoir 204. First pump assembly MP1 can also be operated in forward flow mode to pump the sample stream through feed conduit 103 when the second and third valve assemblies PV5 and PV6 are closed.

In another aspect, the system and method comprise a self-calibration unit as depicted in FIG. 2. The self-calibration unit comprises a calibrating conduit 301 in fluid communication with a calibration fluid source CS which contains a calibration solution, such as a known mixture of ammonium and nitrate/nitrite useful for calibrating the reducing columns RC1-RC4, the first conductivity detector assembly D1, the second conductivity detector assembly D2, or combinations thereof. Calibrating conduit 301 is in further fluid communication with the feed conduit 103. A second one-way valve assembly CV2 configured to open to the flow of calibrating solution from CS to the calibrating conduit 103 but not to reverse flow from the calibrating conduit 103 to source CS. Calibrating valve assembly PV7 is configured to open the flow from calibrating conduit 301 to feed conduit 103 downstream from PV7. In one non-limiting operation, calibrating valve assembly PV7 is open and first pump assembly MP1 pumps calibrating solution from CS downstream to the reducing columns and the conductivity detectors which can then be calibrated.

The pump assemblies designated MP herein can comprise without limitation mini single channel stepper peristaltic pumps as known in the art. The valve assemblies designed PV can comprise without limitation dual channel pinch valves as known in the art.

Gas-diffusion cells useful in the present disclosure for DC1 and DC2 are known in the art including without limitation as described by P. O. J. Hall et al., "Rapid Small-Volume, Flow Injection Analysis for TCO$_2$ and NH$_4^+$ in Marine and Freshwaters" *Limnol. Oceanogr.* 1992, 37(5), 1113-1119.

The detection system and method of the disclosure provides the following: high accuracy and precision during long-term deployment; high selectivity for nitrate/nitrite and ammonium, with no interferences from color, turbidity, and the high concentration hydrate cations and anions in the wastewater sample; a wide response range, including e.g. a response range of 2-70 N-mg/L to greater than 100 N-mg/L; fast and real-time measurement wherein the nitrate/nitrite and ammonium concentrations are in-situ detected and the data can be read in 10-15 min when sample is loaded; continuous and automatic measurement where the sensor package can be remotely and automatically operated, and the data can be remotely transmitted; long-time continuous deployment and long lifetime; high stability and low maintenance; and simultaneous measurement of nitrate/nitrite and ammonium in a single sensor package.

Without limitation, the detection system and method disclosed herein is useful to measure nitrate/nitrite and ammonium/ammonia in various settings, including without limitation, surface water, ground water, wastewater, water treatment plants, septic systems, as well as in laboratory for nitrogen measurement in various research fields. It can be employed in advanced septic systems including innovative/alternative onsite wastewater treatment systems (I/A OWTS) designed to remove significant amounts of nitrogen. as well as in the fields of biology, food technology and clinical settings.

EXAMPLE 1

Figure 3:
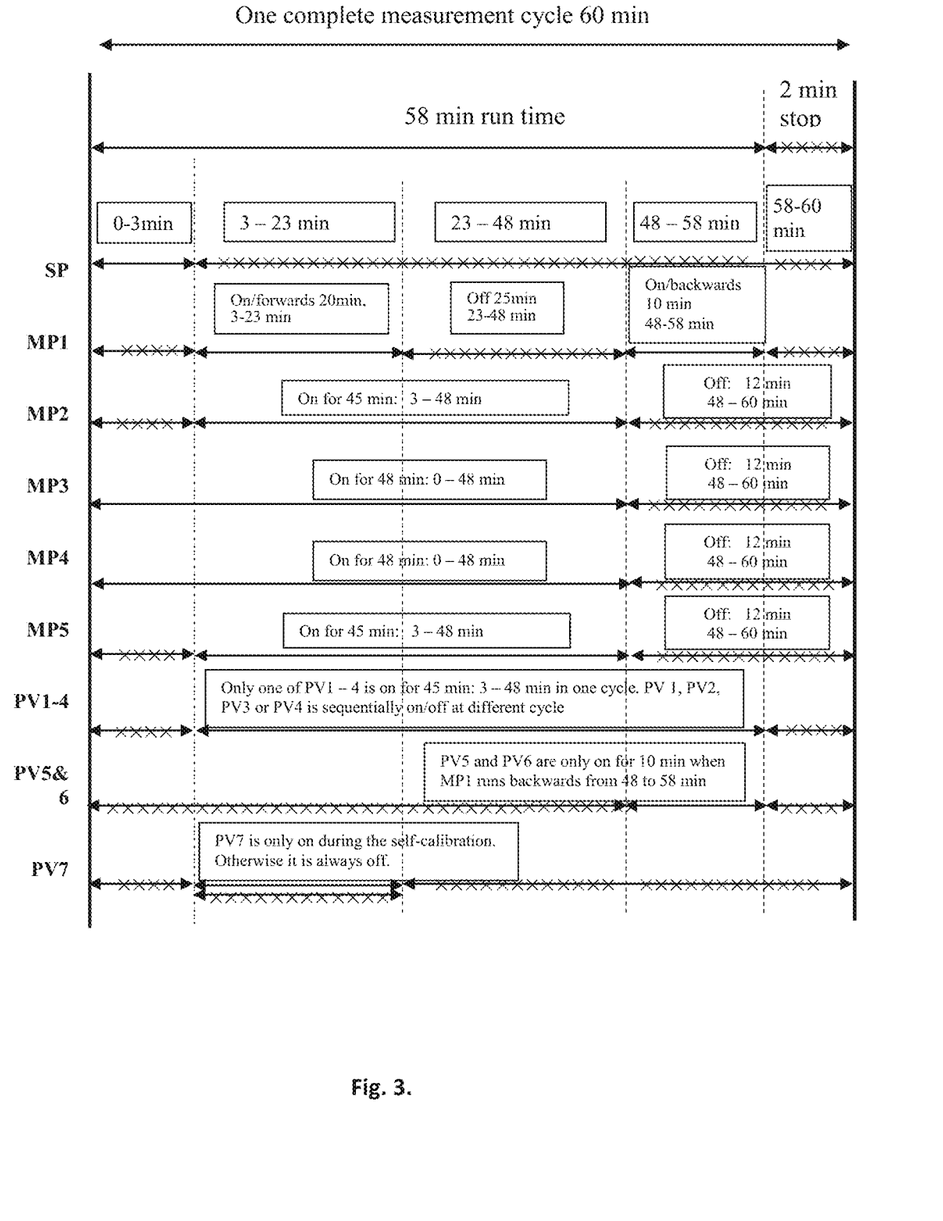
FIG. 3 is an embodiment of operative running times for the pumps and valves for one complete measurement cycle employable in the system of FIG. 1.

General System Setup and Detection Procedures:

The detection system used is as shown in FIG. 1. The system included one DC brushed motor OEM sampling pump (SP, 12V), five single-channel mini stepper OEM peristaltic pumps (MP1, MP2, MP3, MP4 and MP5, 12V) and seven dual-channel pinch valves (PV1, PV2, PV3, PV4, PV5, PV6 and PV7, 12V) which control solution flow and reaction. One complete measurement cycle was set for 60 min and the detailed running time of each pump and pinch valve are summarized in FIG. 3. All pinch valves were turned off at the beginning of a measurement cycle, the sampling pump (SP) started at time zero (t=0 min) and ran at a flow rate of 100 mL/min for 3 min then stopped, circulating and loading the wastewater into the sample loop 101. Meanwhile, the mini pumps MP3 and MP4 were turned on at time t=0 to clean the conductivity probes D1 and D2 and remove any residuals from last measurement using acid solution streams 111 and 112, respectively. The setup and working principle of the sampling system are described in the section of "Wastewater sampling".

At time t=3 min, all mini pumps MP1, MP2, MP3, MP4 and MP5 were on and ran at flow rate of 0.1 mL/min except MP5 which ran at flow rate of 0.2 mL/min. Only one pinch valve among PV1, PV2, PV3 and PV4 was switched on at t=3. The wastewater sample (S) stream was loaded into the feed conduit 103 at continuous flow MP1 for 20 min and mixed with the strong alkaline stream 110 loaded by MP2 at a constant flow rate. The mixture flowed through a polyethylene filter F1 to remove any particles >20 µm. Ammonium cation in the sample was converted to dissolved ammonia gas by the strong alkaline solution in stream 105 and delivered into one side of a gas-diffusion cell DC1, meanwhile a receiving acid solution stream 111 was delivered into the other side of the gas-diffusion cell DC1. Dissolved ammonia gas in the strong alkaline solution stream 105 diffused through a gas-permeable membrane in DC1 and was thus transferred into the receiving acid solution 111 on the other side of the gas-permeable membrane when the acid and base solutions pass over the membrane. Hydrophobic expended PTFE membrane with pore size of 0.2-0.45 micrometer was used as the gas-permeable membrane. Dissolved ammonia gas in alkaline solution stream 105 is completely transferred into the receiving acid solution 111 when the flow rate is less than 0.1 ml/min and gas-diffusion channel in the gas diffusion cell within which sits the gas permeable membrane is 20 cm or longer. Stream 115 was then flowed through conductivity probe detector D1 to determine ammonium concentration which is proportional to the conductivity decrease of the receiving acid stream. The alkaline sample stream 106 exiting the gas-diffusion cell DC1 was collected in a micro reservoir 114 (100 microliter) and was instantaneously pumped by MP5 through a reduction column (one of RC1, RC2, RC3 RC4) to reduce the nitrate and/or nitrite into ammonia in strong alkaline solution. The on/off switch sequence of reduction columns is described in the section of "Reduction column". Once the remaining alkaline sample stream 106 flows through a reduction column, nitrate and/or nitrite in the sample were reduced into ammonia. The alkaline sample stream 108 is then delivered into gas-diffusion cell DC2, identical to DC1, and passed over a gas-permeable membrane on the other side of which is a receiving acid reagent stream 112. The transferred ammonium (from nitrate/nitrite reduction) in receiving acid stream 109 was delivered through the conductivity detector probe D2 to quantify the concentration of nitrate and/or nitrite. Because the wastewater sample matrices can be efficiently blocked by the gas-permeable, liquid-impermeable membrane, the system showed a high selectivity to ammonium and nitrate/nitrite and was free from the interferences of any hydrated cations and anions in the wastewater sample.

At time t=23 min, sample loading mini pump MP1 stopped but pumps MP2, MP3, MP4 and MP5 continually ran for 25 min more at flow rate of 0.1 ml/min to deliver alkaline and acid solutions until the nitrate/nitrite and ammonium signals reached the baseline and become constant at time t=48 min.

At time t=48 min, pumps MP2, MP3, MP4 and MP5 stopped. The backflush flow line was opened by switching on the pinch valves PV5 and PV6, and pump MP1 started to run backwards for 10 min to remove any particles on filter F1 and biofilms in the sampling line. The details of backflush is described in the section of "Wastewater sampling". All pinch valves and pumps were stopped at time t=58 min. The electric control board self-check then started at t=58 min and stopped at time t=60 min, and the system was ready for next cycle measurement.

The system depicted in FIGS. 1 and 2 incorporates a self-calibration unit that was controlled by pinch valve PV7. PV7 automatically switched on after every 20 measurement cycles to calibrate the reduction columns and conductivity probes, otherwise it was always off during the measurement of wastewater sample. When PV7 was switched on, the self-calibration channel 301 was open but the sample loading feed conduit 103 was closed so that only the standard calibration solution was loaded downstream into the detection system. During the self-calibration, the running time schedules for all pumps and pinch valves were the same as that of sample measurement except for PV7. When self-calibration was completed, PV7 was switched off and kept off during the measurement of wastewater sample.

Chemical solutions: the first and second acid feeds 111 and 112 each comprised an acid solution which was 10 mM oxalic acid in distilled water. Alkaline solution feed 110 was an alkaline solution made from 2.5% of potassium hydroxide in distilled water if the sensor was used for measuring nitrate and ammonium in fresh surface water, tap water and ground water. Chelates such as 1% of diethylenetriaminepentaacetic acid (DPTA) or ethylenediaminetetraacetic acid (EDTA) were added into the alkaline solution feed 110 to chelate cations if the sensor was used in wastewater samples. The reduction columns RC1-RC4 comprised granular zinc metal coated with copper such as $CuSO_4$. Granular zinc metal coated with $CuSO_4$ is known in the art, e.g. R. M. Carlson, "Continuous Flow Reduction of Nitrate to Ammonia with Granular Zinc" *Anal. Chem.* 1986, 58, 1590-1591.

Wastewater Sampling:

The setup of the sampling system is shown in FIG. 1. As above, it comprises a "C" shaped sample loop comprising a copper tube of 0.25 in inner diameter with volume of ~10 mL, a DC brushed motor OEM mini pump SP, one mini stepper motor OEM peristaltic pump MP1, and two pinch valves PV5 and PV6. The inlet and outlet of copper tubing were covered by copper screen having a pore size <100 mesh to remove the big particles in wastewater from source S.

At the beginning of a measurement cycle, pinch valves PV5, PV6 and mini pumps (MP1, MP2) were switched off, the wastewater sample was circulated by the sampling pump SP for 3 min at flow rate of 100 ml/min so that the water sample in the source S was well mixed before it was loaded into the feed conduit 103. The sampling pump SP was configured to run alternate forward and backwards in different measurement cycles to remove the particles accumulated on the copper screen. The copper metal tubing 101, screen and sample loop can efficiently inhibit the biofilm formation in the tubing. A copper check-valve CV connected the sample loop 101 to prevent water sample contamination caused by the backflow of any chemical reagents in the system. At time t=3 min, the sampling pump SP stopped and the mini pumps MP1 and MP2 started to load water sample from sample loop 101 and load alkaline solution 110 from a reagent bottle, respectively. The mixed solution 104 passed through a polyethylene filter F1 (pore size <20 μm) and was delivered downstream to the detection units, the particles in mixture larger than 20 μm are caught by filter F1. Pump MP1 ran (0.1 mL/min) for 20 min to load the sample and stopped at time t=23 min, pump MP2 ran (0.1 mL/min) for 45 min to load alkaline solution 110 and stopped at time t=48 min. At time t=48 min, pinch valves PV5 and PV6 were switched on to open the backflush channel 205 and 206 and close the flow of alkaline stream 110 and the flow in the filtered first stream 105, respectively; mini pump MP1 was switched on but ran backwards for 10 min, and was stopped at time t=58 min. The backflush solution (2.5% KOH with 1% chelate DPTA or EDTA) was pumped to backflush the filter F1 and any sampling rubber tubing lines, removing the particles and biofilm on filter F1 and rubber tubing. The particles were then collected by a filter F2 (id: 2-5 cm) and the backflush solution flowed back to the reservoir 204 for recycling use.

Reducing Columns:

The detection system incorporates a robust reduction section comprised of a plurality of reduction columns RC1, RC2, RC3, RC4 as shown in FIG. 1 which permits long-term nitrate/nitrite reduction insofar as the amount of Zn/Cu reducing metal particles in the reduction columns suffice for at least 3-months of system running time. Given that the maximum volume of a reduction column cannot exceed 1 mL in order to obtain a sufficient signal of nitrate/nitrite measurement as due to the slow flow rate of sample solution in the system. Thus a plurality of reduction columns arranged for parallel flow as shown in FIG. 1 were employed. The inlet for each individual reduction column was controlled by a pinch valve, i.e. reduction columns RC1, RC2, RC3, RC4 are controlled by valves PV1, PV2, PV3, PV4, respectively. Only one of these four pinch valves was on during one measurement cycle from time t=3-58 min and then switched off at time t=58 min. The pinch valve PV1, PV2, PV3 or PV4 is sequentially turned on in different measurement cycles, so the reduction columns RC1-RC4 in FIG. 1 were sequentially and alternately used. Consumption of the Zn/Cu particles disposed within each reduction column was comparable and the performance of all the four columns was identical even after the system continuously ran for 3 months in the wastewater.

EXAMPLE 2

Real-Time Sensor Data for Ammonium, Nitrate/Nitrite Measurement in Wastewater

Two detection systems as depicted in FIG. 1 and described in Example 1 were installed and continuously operated in the wastewater sample reservoir at the Massachusetts Alternative Septic System Test Center (MASSTC) and automatically run for one-month. The systems were controlled and operated remotely, the concentrations of nitrate/nitrite and ammonium were measured hourly and the data was remotely saved and transferred. The system was required to continuously deploy in wastewater and recorded 704 readings of ammonium and nitrate/nitrite data. Meanwhile, 57 lab samples were taken from the reservoir and analyzed in a certified lab.

Figure 4:
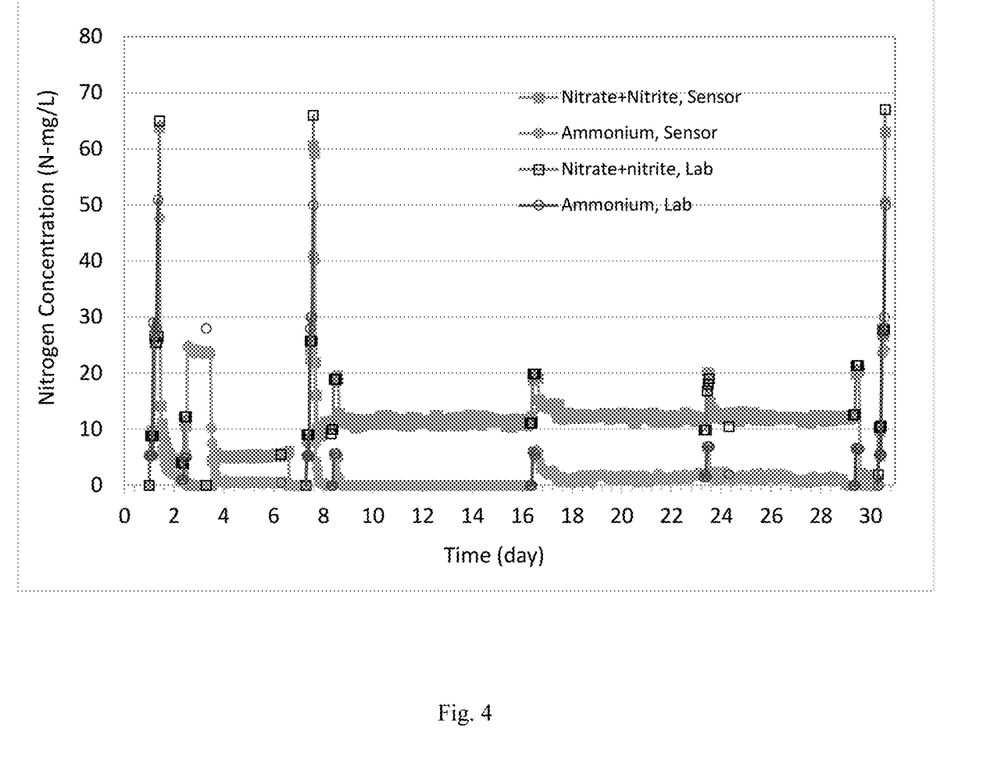
FIG. 4 is a graph comparing real-time response of the detection system of the disclosure as against lab data.

At the end of the one-month test, the in-situ data obtained from the detection system of the disclosure was compared with the data from the certified lab. The results, shown in FIG. 4, were submitted to the EPA and show that the detection system of the disclosure met all the performance parameters set by the EPA for detection. The relative standard deviation (RSD) of sensor in-situ measurement was <±10% and the accuracy was in the range of 80-120% recovery for both ammonium and nitrate/nitrite in the one-month field test. The Average recovery of one-month test was >95% for both ammonium and nitrate.

What is claimed is:

1. A detection system for simultaneously determining the concentration of ammonium, nitrate/nitrite in a wastewater sample comprising:
    a sample loop having an internal flow path in fluid communication with a wastewater sample comprising water, ammonium, nitrate/nitrite, and particulate matter, the sample loop comprising a loop outlet in fluid communication with a feed conduit, a first one-way valve assembly configured to be open to the feed conduit, and a first pump assembly in fluid communication with the feed conduit;

a first alkaline stream in fluid communication with the feed conduit to mix the first alkaline solution with the wastewater sample and convert the ammonium to ammonia and generate a first stream;

a first filter assembly in fluid communication with the first stream to remove at least a portion of the particulate matter from the sample stream and generate a filtered first stream;

a first gas-diffusion cell comprising a first acid solution feed for (i) removing the ammonia from the filtered first stream to generate second stream comprising the nitrate/nitrite and for (ii) converting the removed ammonia back to ammonium to generate a third stream comprising the ammonium a first conductivity detector assembly for determining the concentration of ammonium in the third stream;

a plurality of reducing columns, each reducing column individually comprising a reducing metal to convert the nitrate/nitrite in the second stream to ammonia and to generate a fourth stream comprising the ammonia produced by reducing the nitrate/nitrite, the plurality of reducing columns configured for parallel flow, and a valve assembly for each of the reducing columns configured open the flow of the second stream to the respective reducing columns one at a time;

a second gas-diffusion cell comprising a second acid solution feed for (i) removing the ammonia produced by reducing the nitrate/nitrite in the fourth stream and (ii) converting the removed ammonia produced by reducing the nitrate/nitrite back to ammonium to generate a fifth stream comprising the ammonium;

a second conductivity detector assembly for determining the concentration of ammonium in the fifth stream from which the concentration of the nitrate/nitrite is determined.

2. The detection system of claim 1 further comprising a recycle cleaning loop in fluid communication with the first filter assembly, the cleaning loop configured to provide a reverse flow of a backflush solution through the first filter assembly and when the first valve assembly is in the closed position.

3. The detection system of claim 2 wherein the recycle cleaning loop comprises: a reservoir containing a backflush solution; a backflush feed conduit in fluid communication with the reservoir and the first filter assembly; a backflush recycle conduit in fluid communication with the feed conduit and with the backflush reservoir or a recycle storage reservoir; and a second valve assembly configured to open and close the flow of backflush solution from the backflush feed conduit to the filter assembly.

4. The detection system of claim 3 further comprising a second filter assembly in fluid communication with the backflush recycle conduit to remove particulate matter from the backflush solution returning to the reservoir or the recycle storage reservoir; and a third valve assembly configured to open the flow of backflush solution from the backflush recycle conduit to the second filter assembly.

5. The detection system of claim 1 wherein the first pump assembly is in fluid communication with the backflush feed conduit when the second valve assembly and the third valve assembly are in the open position, the first pump assembly configured to provide the reverse flow of the backflush solution through the first filter.

6. The detection system of claim 1 further comprising a self-calibration unit comprising: a calibrating conduit in fluid communication with a calibration fluid source containing a calibration solution for calibrating the reduction columns, the first conductivity detector assembly, the second conductivity detector assembly, or combinations thereof, and in fluid communication with the feed conduit; a second one-way valve assembly configured to open the flow of calibrating solution to the feed conduit.

7. The detection system of claim 1 wherein the first alkaline stream comprises NaOH, KOH, or combinations thereof, and optionally comprises one or more chelates selected from diethylenetriaminepentaacetic acid (DPTA), ethylenediaminetetraacetic acid (EDTA, or both.

8. The detection system of claim 1 wherein the first and second gas-diffusion cells each individually comprise a gas permeable membrane comprised of a hydrophobic expended PTFE membrane comprising a pore size of 0.2-0.45 micrometer and a thickness of greater than 60 micrometers.

9. The detection system of claim 1 wherein the first and second acid feeds comprise oxalic acid, citric acid, or HCl.

10. The detection system of claim 1 wherein the reducing metal comprises granular zinc coated with 5% $CuSO_4$.

11. The detection system of claim 1 further comprising an intermediate reservoir to collect the second stream generated by the first gas-diffusion cell and a third pump assembly in fluid flow communication with the intermediate reservoir and the plurality of reducing columns.

12. A method for simultaneously determining the concentration of ammonium and nitrate/nitrite in a sample comprising:

(a) providing a sample loop having an internal flow path and comprising a loop outlet in fluid communication with a feed conduit, and a first one-way valve assembly configured to be open to the feed conduit;

(b) flowing a sample stream comprising water, ammonium, and nitrate/nitrite, and particulate matter, from the loop outlet through the feed conduit using a first pump assembly, the first one-way valve assembly being in an open position;

(c) converting the ammonium in the sample stream to ammonia to form a first stream comprising the ammonia and the nitrate/nitrite;

(d) flowing the first stream through a first filter assembly to remove at least a portion of the particulate matter from the first stream and generate a filtered first stream;

(e) removing the ammonia from the filtered first stream to form a second stream comprising the nitrate/nitrite;

(f) converting the removed ammonia back to ammonium to form a third stream comprising the ammonium and determining the concentration of ammonium in the third steam; and (g) reducing the nitrate/nitrite in the second stream to ammonia to form a fourth stream comprising the ammonia produced by reducing the nitrate/nitrite and converting the ammonia in the fourth stream to ammonium to form a fifth stream comprising the ammonium that was converted from the ammonia in the fourth stream, and determining the concentration of the ammonium in the fifth stream to determine to the concentration of the nitrate/nitrite.

13. The method of claim 12 wherein in step (g) the molar concentration of the nitrate/nitrite is equal to the molar concentration of the ammonium in the fifth stream.

14. The method of claim 12 wherein the sample loop comprises a first loop opening and a second loop opening, each in fluid communication with a sample source; and the first pump assembly is in fluid communication with the first and second loop openings, the first pump assembly configured to provide forward and reverse flow, wherein at least a portion of the forward flow provides sample from the first loop opening to the loop outlet, and wherein at least a portion of the reverse flow provides sample from the second loop opening to the loop outlet.

15. The method of claim 14 wherein the sample loop comprises copper tubing; and the first loop opening and the second loop opening each individually comprise a copper screen.

16. The method of claim 15 wherein at least a portion of the forward flow traverses the internal pathway and exits the second loop opening to remove particulate matter from the opposite side of the respective copper screen; and wherein at least a portion of the reverse flow traverses the internal pathway and exits the first loop opening to remove particulate matter from the opposite side of the respective copper screen.

17. The method of claim 12 further comprising providing a recycle cleaning loop in fluid communication with the feed conduit and the first filter assembly, the cleaning loop configured to provide a reverse flow of a backflush solution through the first filter assembly and the feed conduit when the first valve assembly is in the closed position.

18. The method of claim 17 wherein the recycle cleaning loop comprises:
a reservoir containing a backflush solution; a backflush feed conduit in fluid communication with the reservoir and the first filter assembly; a backflush recycle conduit in fluid communication with the feed conduit and with the backflush reservoir or with a recycle storage reservoir; and a second valve assembly configured to open the flow of backflush solution from the backflush feed conduit to the first filter assembly.

19. The method of claim 18 further comprising: a second filter assembly in fluid communication with the backflush recycle conduit to remove particulate matter from the backflush solution returning to the reservoir or the recycle storage reservoir; and a third valve assembly configured to open the flow of backflush solution from the backflush recycle conduit to the second filter assembly.

20. The method of claim 19 wherein the first pump assembly is in fluid communication with the backflush feed conduit when the second valve assembly and the third valve assembly are in the open position, the first pump assembly configured to provide the reverse flow of the backflush solution through the feed conduit.

21. The method of claim 12 wherein reducing the nitrate/nitrite in the second stream comprises feeding the second steam to a plurality of reducing columns, each reducing column individually comprising a reducing metal to convert the nitrate/nitrite in the second stream to ammonia to generate the fourth stream, the plurality of reducing columns configured for parallel flow, each of the reducing columns comprising a reducing column valve assembly to open or stop the flow of the second stream to one of the respective reducing columns; and wherein the determining the concentration of the ammonium in the third steam is by a first conductivity detector assembly, and the determining the concentration of the ammonium in the fifth stream is by a second conductivity detector assembly.

22. The method of claim 21 comprising operating the reducing column valve assemblies to cycle flow of the second stream to one reducing column at a time.

23. The method of claim 22 wherein each cycle is for the same pre-determined time and the cycle flow follows the sequence of reducing columns in the parallel flow configuration.

24. The method of claim 12 further comprising providing a self-calibration unit comprising:
a calibrating conduit in fluid communication with a calibration fluid source containing a calibration solution for calibrating the reducing columns, the first conductivity detector assembly, the second conductivity detector assembly, or combinations thereof, the calibrating conduit in further fluid communication with the feed conduit; and a second one-way valve assembly configured to open the flow of calibrating solution to the feed conduit.

25. The method of claim 12 wherein the ammonium in the sample stream is converted to ammonia to form the first stream by contacting the ammonium with an alkaline stream comprising an alkaline selected from NaOH, KOH, or combinations thereof, the alkaline stream provided by a second pump assembly.

26. The method of claim 12 wherein the ammonia is removed from the filtered first stream in step (e) and converted back to ammonium in step (f) by a first gas-diffusion cell having a first acid solution feed; and the ammonia in the fourth stream is converted to ammonium in step (g) by a second gas-diffusion cell having a second acid solution feed, the first and second gas-diffusion cells being the same or different design, and the first and second acid solution feeds being the same or different.

27. The method of claim 26 wherein the first and second gas-diffusion cells are of the same design and the first and second acid feeds each independently comprise oxalic acid, citric acid, or HCl.

28. The method of claim 21 further comprising collecting the second stream in a intermediate reservoir, and pumping at least a portion of the collected second stream from the intermediate reservoir to the plurality of reducing columns.

* * * * *